(12) United States Patent
Ishizaki et al.

(10) Patent No.: US 9,888,989 B2
(45) Date of Patent: Feb. 13, 2018

(54) INTAKE DEVICE

(71) Applicants: KABUSHIKI KAISHA SANGI, Tokyo (JP); TOHOKU UNIVERSITY, Sendai-shi, Miyagi (JP)

(72) Inventors: Tsutomu Ishizaki, Tokyo (JP); Kazushi Ohta, Tokyo (JP); Shuji Sakuma, Tokyo (JP); Tsunemoto Kuriyagawa, Sendai (JP)

(73) Assignees: KABUSHIKI KAISHA SANGI (JP); TOHOKU UNIVERSITY (JP)

( * ) Notice: Subject to any disclaimer, the term of this patent is extended or adjusted under 35 U.S.C. 154(b) by 0 days.

(21) Appl. No.: 14/779,745

(22) PCT Filed: Apr. 17, 2014

(86) PCT No.: PCT/JP2014/061502
§ 371 (c)(1),
(2) Date: Sep. 24, 2015

(87) PCT Pub. No.: WO2014/171555
PCT Pub. Date: Oct. 23, 2014

(65) Prior Publication Data
US 2016/0100922 A1 Apr. 14, 2016

(30) Foreign Application Priority Data

Apr. 18, 2013 (JP) ................. 2013-087134

(51) Int. Cl.
*A61C 17/06* (2006.01)
*A61G 15/14* (2006.01)
(Continued)

(52) U.S. Cl.
CPC ............ *A61C 17/043* (2013.01); *A61C 17/04* (2013.01); *A61G 15/14* (2013.01); *B08B 15/04* (2013.01); *F24F 2013/088* (2013.01)

(58) Field of Classification Search
CPC .................... A61C 17/043; A61C 17/04
See application file for complete search history.

(56) References Cited

U.S. PATENT DOCUMENTS

D287,402 S  *  12/1986  Orsing ............................ 433/91
4,776,793 A  *  10/1988  La Rocca ............ A61C 17/043
                                                        433/96

(Continued)

FOREIGN PATENT DOCUMENTS

DE      29900106 U1    4/1999
JP      S49-096752 U   8/1974
(Continued)

OTHER PUBLICATIONS

Extended European Search Report for Patent Application No. EP14786090.2 dated Dec. 9, 2016 (7 pages).

*Primary Examiner* — Cris L Rodriguez
*Assistant Examiner* — Hao D Mai
(74) *Attorney, Agent, or Firm* — Harness, Dickey & Pierce, P.L.C.

(57) ABSTRACT

Due to the low suction strength or an unsuitable positional relationship or distance between the suction feed and the oral cavity, conventional extra-oral intake devices exhibit the problem of not being able to fully suck particulate matter and droplets from teeth, shavings from repair products, saliva, bacteria, blood, rinse water, tooth surface cleaning agents, etc., that are dispersed to outside the oral cavity during practice. In order to improve suction strength, the present invention provides an intake device that is equipped with a protruding airflow-regulating member, the top of which is oriented in the direction in which the fluid flows into the opening part of the suction feed, and that can efficiently suck dispersed particulate matter and droplets within a wide range.

20 Claims, 13 Drawing Sheets

(51) Int. Cl.
  *B08B 15/04* (2006.01)
  *F24F 13/08* (2006.01)

(56) References Cited

U.S. PATENT DOCUMENTS

| | | | |
|---|---|---|---|
| 4,865,545 A * | 9/1989 | La Rocca | A61C 17/043 433/96 |
| D312,872 S * | 12/1990 | Mahl | D24/112 |
| 6,186,783 B1 * | 2/2001 | Brassil | A61C 17/043 433/91 |
| 6,308,707 B1 | 10/2001 | Lu | |
| 6,332,837 B1 * | 12/2001 | Wilk | B08B 15/04 219/137.41 |
| 6,776,710 B1 * | 8/2004 | Messmer | F24F 13/06 34/97 |
| 7,238,023 B1 * | 7/2007 | Enos | A61C 17/043 433/91 |
| 7,625,207 B2 * | 12/2009 | Hershey | A61C 1/16 433/100 |
| 8,398,398 B1 * | 3/2013 | Barham | A61C 17/043 433/91 |
| 2003/0029321 A1 * | 2/2003 | Mishin | B01D 46/0005 96/142 |
| 2005/0096608 A1 * | 5/2005 | Mannschedel | A61C 17/043 604/264 |
| 2009/0204065 A1 * | 8/2009 | Wright | A61M 1/008 604/35 |
| 2010/0115896 A1 * | 5/2010 | Reid | B08B 15/04 55/356 |
| 2011/0262880 A1 * | 10/2011 | McCary | A61C 17/04 433/92 |
| 2013/0196585 A1 * | 8/2013 | Hedlund | B08B 15/04 454/63 |
| 2015/0209562 A1 * | 7/2015 | Harari | A61B 17/0218 604/21 |

FOREIGN PATENT DOCUMENTS

| | | |
|---|---|---|
| JP | S56-109536 U | 8/1981 |
| JP | H07-025537 Y2 | 6/1995 |
| JP | H09-38112 A | 2/1997 |
| JP | 2004-033474 A | 2/2004 |
| JP | 2011-122738 A | 6/2011 |
| JP | 2012-075705 A | 4/2012 |
| JP | 2013-096318 A | 5/2013 |

* cited by examiner

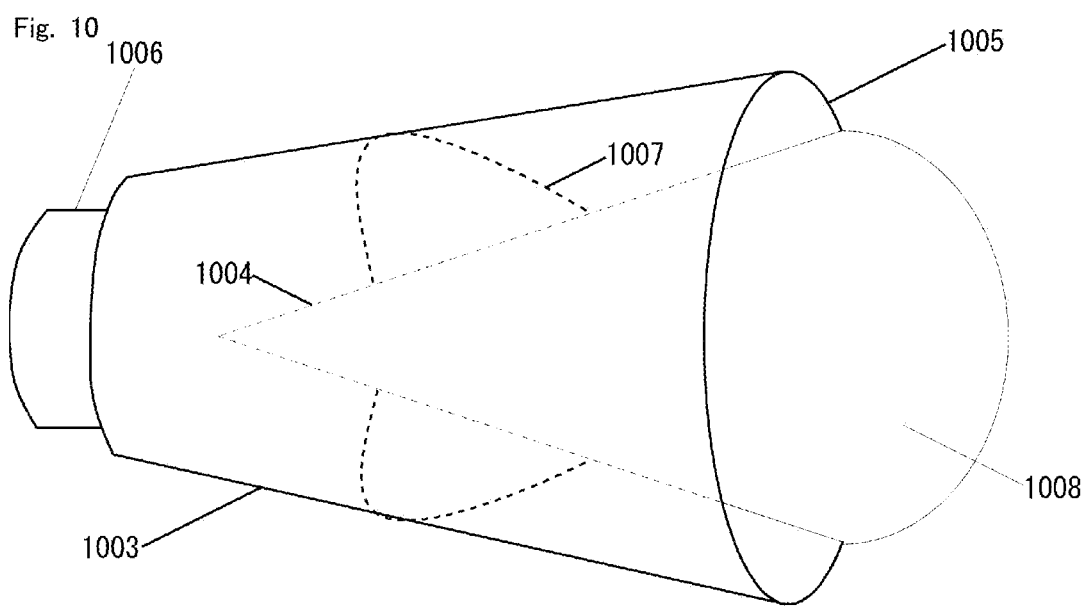

INTAKE DEVICE

CROSS-REFERENCE TO RELATED APPLICATIONS

This application is a U.S. National Phase Application under 35 U.S.C. 371 of International Application No. PCT/JP2014/061502, filed on Apr. 17, 2014 and published in Japanese as WO 2014/171555 A1 on Oct. 23, 2014. This application claims priority to Japanese Patent Application No. 2013-087134, filed on Apr. 18, 2013. The entire disclosures of the above applications are incorporated herein by reference.

BACKGROUND OF THE INVENTION

Technical Field

The present invention relates to an intake device comprising a flow straightening member in an opening part of a suction hood.

Background Art

In dental treatment, an extraoral intake device is used for protecting health of patients and dental medical workers and keeping the inside of an examination room clean by sucking at patients' mouth dust or spray which scatters to the outside of a mouth during the examination, such as shavings of teeth or repairing material, saliva, bacterium, blood, rinse water, cleaning agent for tooth surfaces, and so on.

SUMMARY OF THE INVENTION

Technical Problem

However, in the conventional technique, the above dust or spray cannot be completely sucked because the suction force is weak or because distance or positional relationship between a suction hood and a mouth is not appropriate.

In order to improve suction force, the present invention provides an intake device comprising a flow straightening member in an opening part of a suction hood.

Means for Solving the Problem

Specifically, the present invention provides the following intake device.

In the first invention, an intake device having a suction hood provided with a flow straightening member convex toward a fluid flow direction is provided.

In the second invention, based on the first invention, an intake device wherein the flow straightening member has one kind of shape selected from a generally egg shape, a generally cone shape, a generally pyramidal shape, and a generally partial spherical shape, is provided.

In the third invention, based on either one of the first invention or the second invention, an intake device wherein an inner surface of the suction hood has a megaphone's inner surface shape, is provided.

In the fourth invention, based on any one of the first invention to the third invention, an intake device wherein the flow straightening member is completely housed in the inner space of the suction hood, is provided.

In the fifth invention, based on any one of the first invention to the third invention, an intake device wherein the flow straightening member is arranged to protrude from the inner space of the suction hood, is provided.

In the sixth invention, based on the fifth invention, an intake device wherein the protruding part of the flow straightening member is convex toward the opposite side of a fluid flow direction, is provided.

Advantageous Effects of the Invention

The present invention provides an intake device which can efficiently suck dust or spray scattering widely.

BRIEF DESCRIPTION OF THE DRAWINGS

FIG. 10 is a view enlarging the suction hood part of the intake device in the embodiment 3.

DETAILED DESCRIPTION OF THE PREFERRED EMBODIMENTS

Embodiments of the present invention will be described below by using the attached drawings. The present invention is not limited to the embodiments and can be put into practice in various modes within a range not departing from its gist. An embodiment 1 will be described mainly for claims 1 to 3. An embodiment 2 will be described mainly for claim 4. An embodiment 3 will be described mainly for claims 5 and 6.

Embodiment 1

Embodiment 1: Outline

The intake device in this embodiment is characterized by being provided with a flow straightening member convex toward a fluid flow direction in its suction hood.

Embodiment 1: Structure

Figure 1:
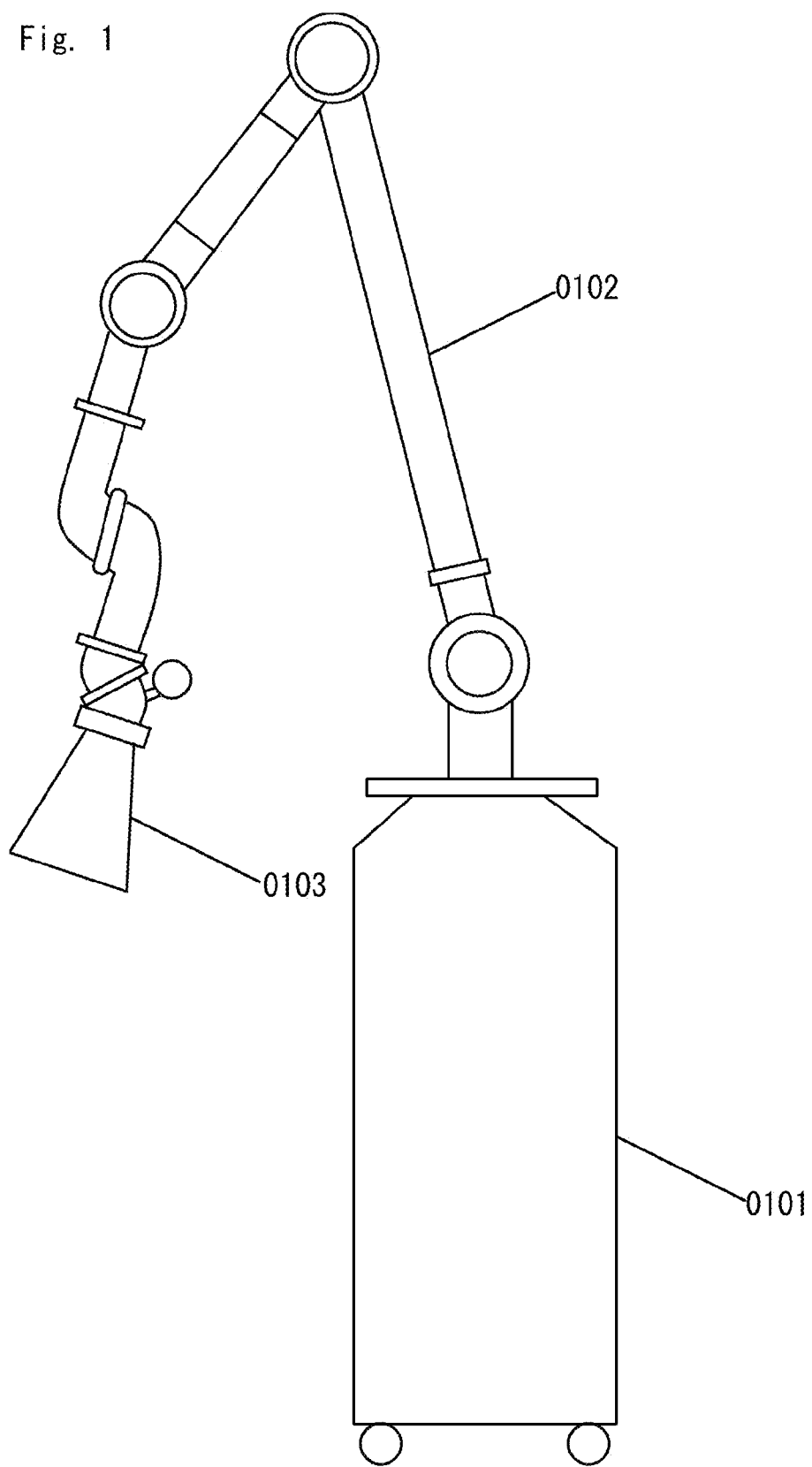
FIG. 1 is a schematic view illustrating a whole of the intake device in the embodiment 1.

The intake device in this embodiment has a suction hood provided with a flow straightening member, and additionally, may have a main body or an arm and the like. FIG. 1 is a schematic view illustrating a whole of the intake device in this embodiment.

The "main body" (0101) is provided with a mechanism which generates negative pressure to perform suction. Specifically, a motor starts rotating when turning on power, and a member connected to a rotary shaft of the motor rotates to generate negative pressure inside the main body.

The "arm" (0102) is a component connected to the main body, having a function for supporting a suction hood which will be explained in detail. As illustrated in FIG. 1, the arm is preferably provided with a plurality of joints. By this configuration, the position of the suction hood connected to the tip of the arm can be easily adjusted.

Figure 2:
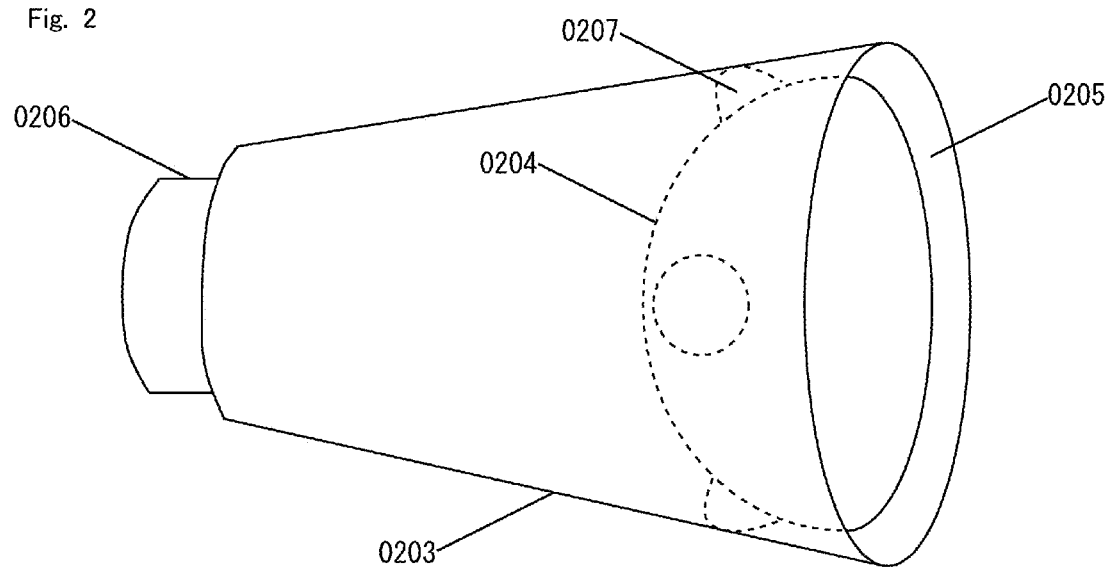
FIG. 2 is a view enlarging the suction hood part of the intake device in the embodiment 1.

The "suction hood" (0103) is a component connected to the tip of the arm, having a function for catching dust or spray. FIG. 2 is a view enlarging the suction hood part of the intake device in this embodiment. The dotted line part illustrates the structure inside the suction hood. As illustrated in FIG. 2, in this embodiment, an inner surface of the suction hood is configured to have a megaphone's inner surface shape. By this configuration, the catching space is made larger and dust or spray scattering widely can be sucked efficiently.

The "flow straightening member" (0204) is a component arranged inside the suction hood, having a function for introducing the air sucked from the suction port (0205) into the cavity. The flow straightening member in this embodiment is characterized by being convex toward a fluid flow direction. As illustrated in FIG. 2, being convex toward a fluid flow direction means being convex toward the exhaust port (0206). The flow straightening member is fixed to the inside of the suction hood by the supporting base (0207).

Figure 3:
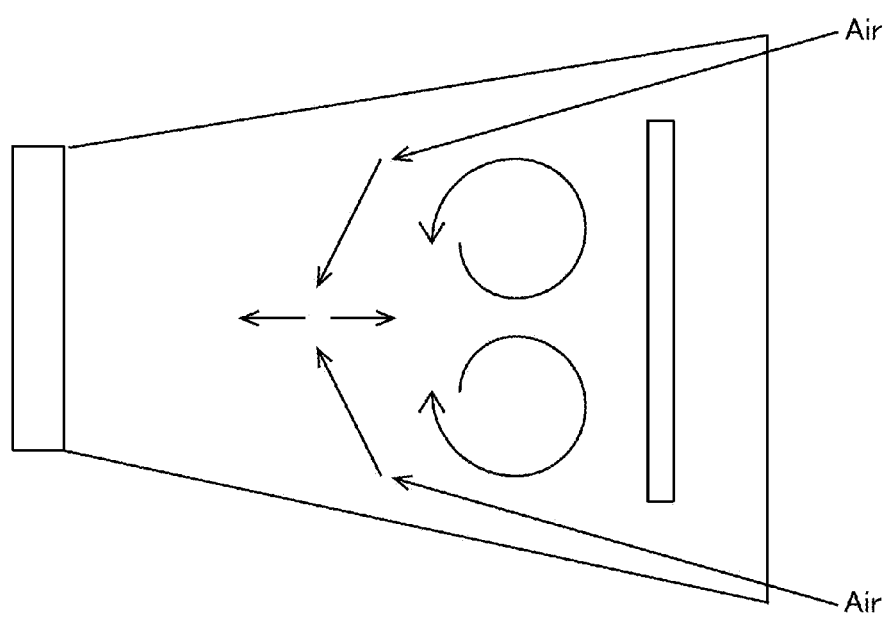
FIG. 3 is a schematic view illustrating the flow straightening in the conventional technique.

FIG. 3 is a schematic view illustrating the flow straightening in the conventional technique. As illustrated in FIG. 3, the flow straightening member in a plate shape as in the conventional technique cannot sufficiently prevent the occurrence of a vortex.

Figure 4:
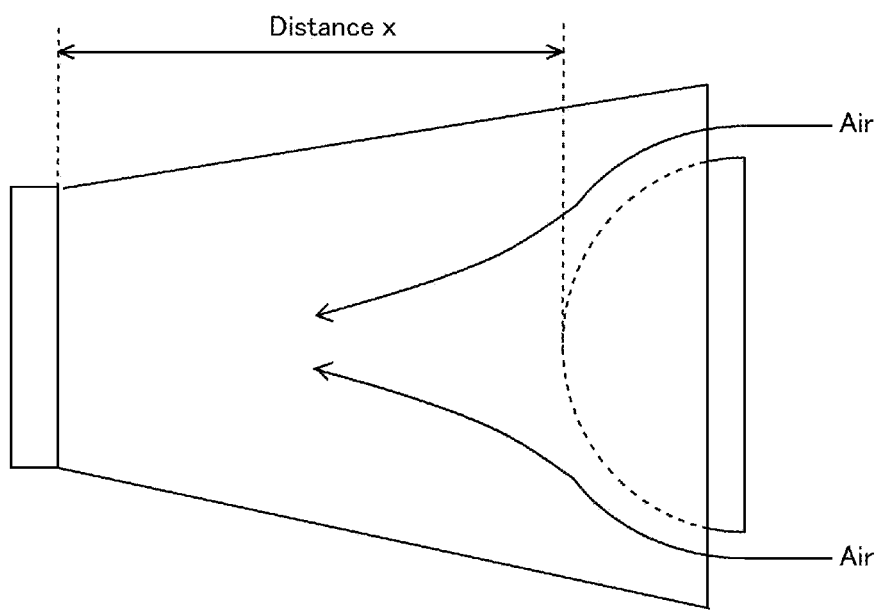
FIG. 4 is a schematic view illustrating the flow straightening in the intake device in the embodiment 1.

FIG. 4 is a schematic view illustrating the flow straightening in the intake device in this embodiment. As illustrated in FIG. 4, in case where the flow straightening member is configured to have a generally partial spherical shape convex toward the exhaust port, the sucked air is introduced along the convex surface. Therefore, it does not generate a vortex and is carried to the exhaust port smoothly. In order to minimize the volume of the catching space where a vortex may occur, the distance x from the end of the flow straightening member to the exhaust port is preferably short.

Figure 5:
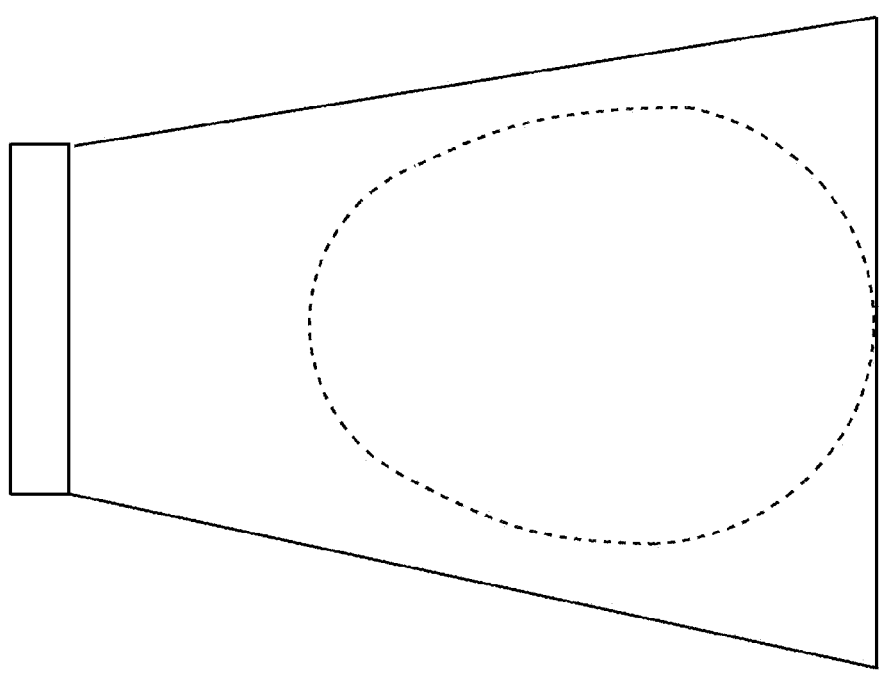
FIG. 5 is a view illustrating an example of the shape of the flow straightening member.
Figure 6:
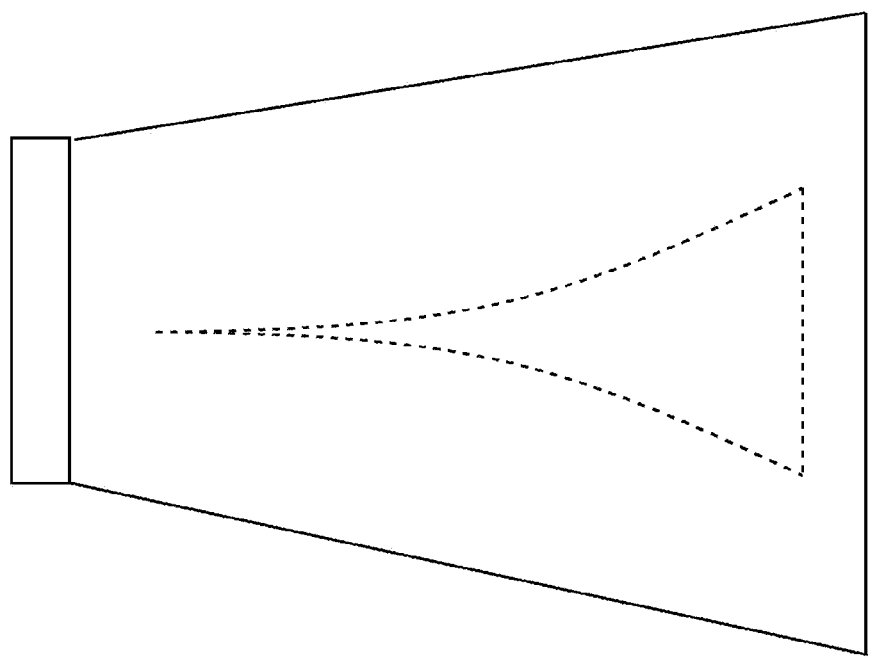
FIG. 6 is a view illustrating an example of the shape of the flow straightening member.
Figure 7:
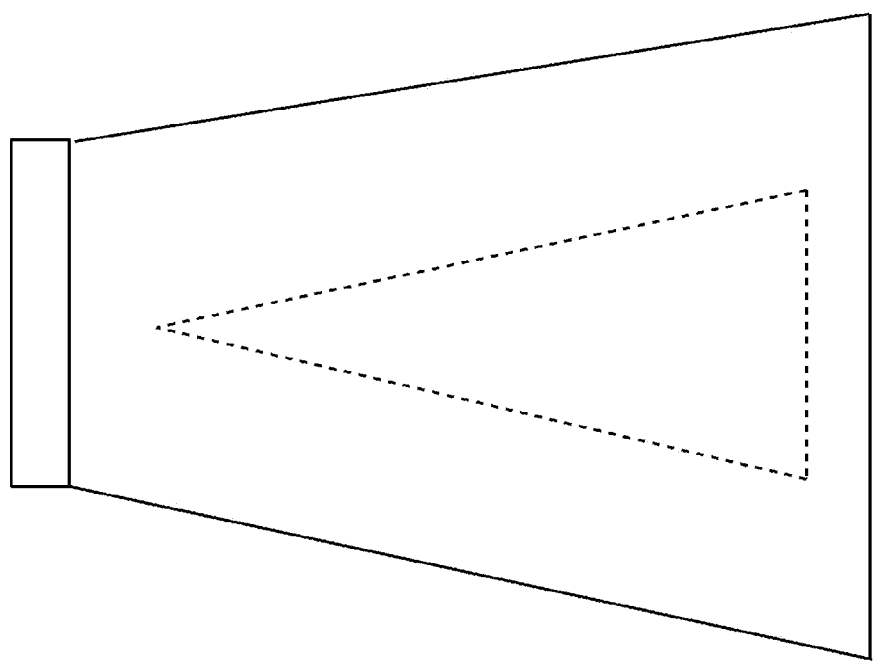
FIG. 7 is a view illustrating an example of the shape of the flow straightening member.

As the shape of the flow straightening member, other than a generally partial spherical shape, it is also considered to take a generally egg shape as illustrated in FIG. 5, or a generally cone shape as illustrated in FIG. 6, or a generally pyramidal shape as illustrated in FIG. 7. In any of the shape, the sucked air is carried to the exhaust port smoothly along the convex surface of the flow straightening member.

Figure 8A:
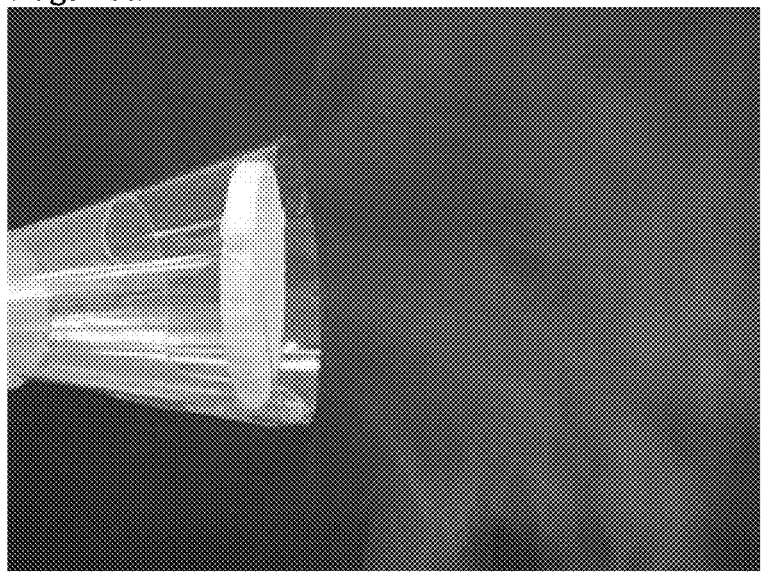
FIG. 8*a* is a photo of the intake device sucking smoke in case where the flow straightening member is configured to be planar.
Figure 8B:
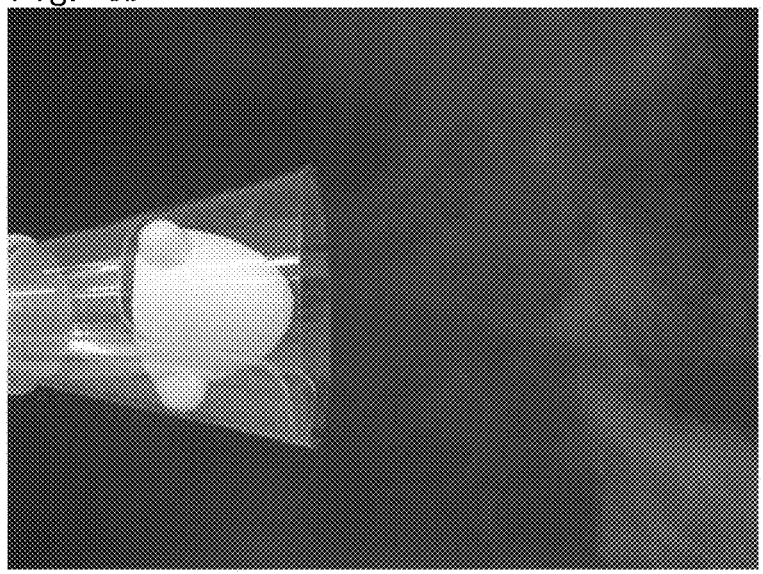
FIG. 8*b* is a photo of the intake device sucking smoke in case where the flow straightening member is configured to be convex toward the opposite side of a fluid flow direction.
Figure 8C:
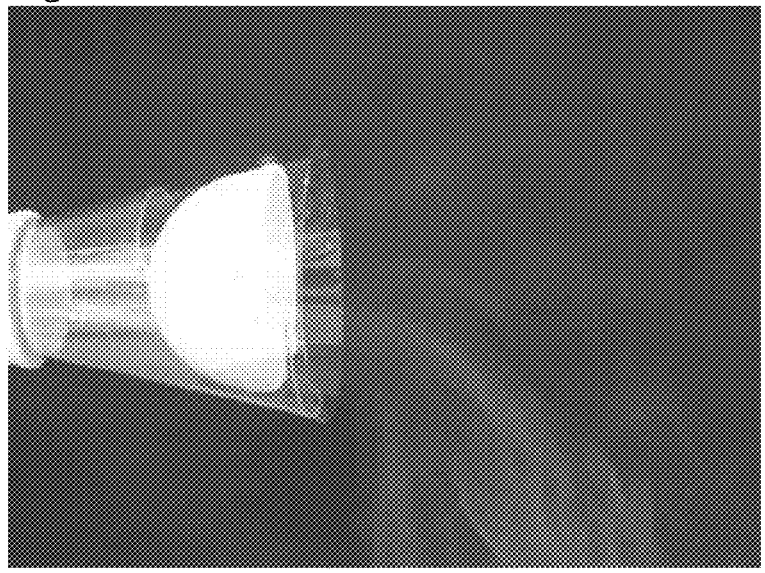
FIG. 8*c* is a photo of the intake device sucking smoke in case where the flow straightening member is configured to have a generally partial spherical shape convex toward a fluid flow direction.
Figure 8D:
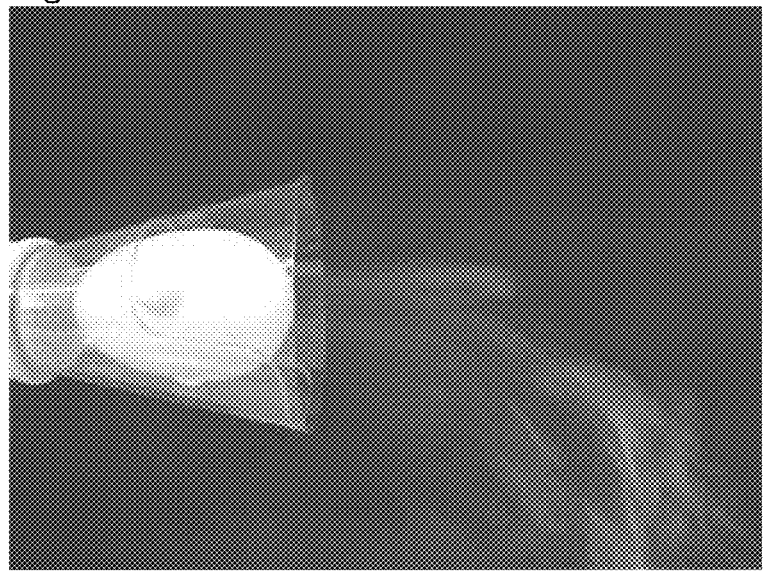
FIG. 8*d* is a photo of the intake device sucking smoke in case where the flow straightening member is configured to have a generally egg shape convex toward a fluid flow direction.

FIGS. 8a to 8d are photos of the intake device sucking smoke. FIG. 8a is a photo in case where the flow straightening member is configured to be planar. FIG. 8b is a photo in case where the flow straightening member is configured to be convex toward the opposite side of a fluid flow direction. FIG. 8c is a photo in case where the flow straightening member is configured to have a generally partial spherical shape convex toward a fluid flow direction. FIG. 8d is a photo in case where the flow straightening member is configured to have a generally egg shape convex toward a fluid flow direction. In FIGS. 8c and 8d, in comparison with FIGS. 8a and 8b, a line of the sucked smoke appears clearly. Therefore, it is shown that the occurrence of a vortex near the exhaust port is prevented and the sucking linear velocity is improved by the flow straightening member configured as in this embodiment.

Embodiment 1: Effects

The present invention provides an intake device which can efficiently suck dust or spray scattering widely.

Embodiment 2

Embodiment 2: Outline

In the intake device in the embodiment 1, in case where a part of the flow straightening member is arranged outside the suction hood, the air introduced along the part does not flow to the exhaust port directly and a part of dust or spray scatters to the vicinity.

The intake device in this embodiment is characterized in that the flow straightening member is completely housed in the inner space of the suction hood in order to solve such a problem.

Embodiment 2: Structure

The intake device in this embodiment comprises a main body, an arm, a suction hood, and a flow straightening member. The main body, the arm, and the suction hood are the same as described in the embodiment 1. The flow straightening member is the same as described in the embodiment 1, except for the following points.

Figure 9:
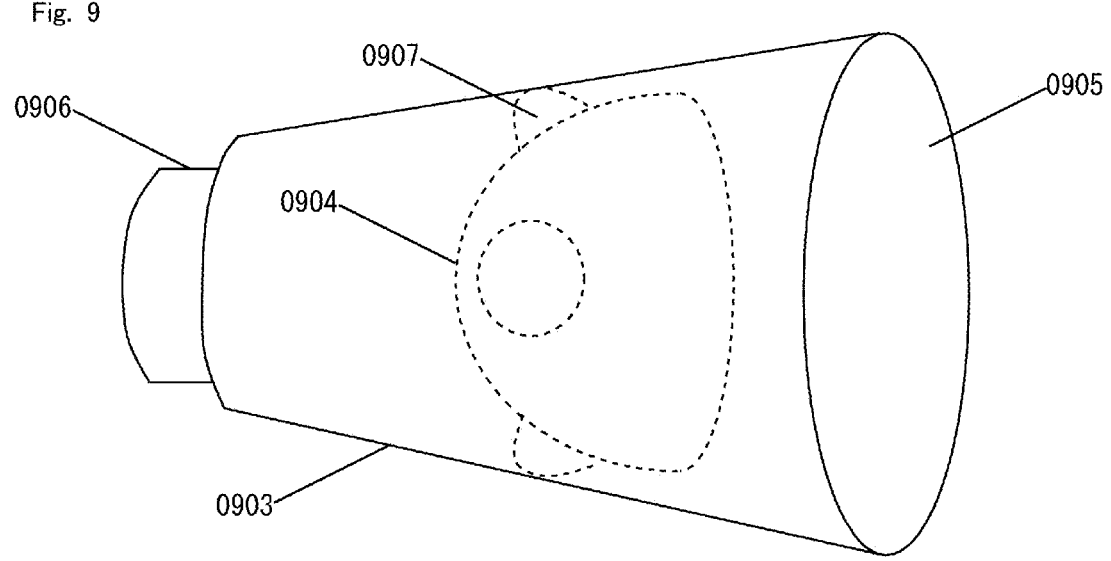
FIG. 9 is a view enlarging the suction hood part of the intake device in the embodiment 2.

FIG. 9 is a view enlarging the suction hood part of the intake device in this embodiment. As illustrated in FIG. 9, the "flow straightening member" (0904) in this embodiment is arranged to be completely housed in the inner space of the suction hood. By this configuration, the air introduced along the convex surface of the flow straightening member wholly flow to the exhaust port and dust or spray can be efficiently sucked.

Embodiment 2: Effects

The present invention provides an intake device which can efficiently suck dust or spray scattering widely.

Embodiment 3

Embodiment 3: Outline

The intake device in this embodiment is characterized in that a part of the flow straightening member is arranged to protrude from the inner space of the suction hood and the protruding part is convex toward the opposite side of a fluid flow direction.

Embodiment 3: Structure

The intake device in this embodiment comprises a main body, an arm, a suction hood, and a flow straightening member. The main body, the arm, and the suction hood are the same as described in the embodiment 1. The flow straightening member is the same as described in the embodiment 1, except for the following points.

FIG. 10 is a view enlarging the suction hood part of the intake device in this embodiment. As illustrated in FIG. 10, the "flow straightening member" (1004) in this embodiment is arranged to protrude from the inner space of the suction hood. The protruding part of the flow straightening member (1008) is configured to be convex toward the opposite side of a fluid flow direction.

In the intake device in this embodiment, for the protruding part of the flow straightening member has a convex shape, the air introduced along the part of the flow straightening member is carried to the inner space of the suction hood smoothly and dust or spray does not scatter to the vicinity. In case where the flow straightening member is configured to have the shape as illustrated in FIG. 10, the distance from the end of the flow straightening member to the exhaust port is made short and the occurrence of a vortex can be prevented more efficiently.

Embodiment 3: Effects

The present invention provides an intake device which can efficiently suck dust or spray scattering widely.

What is claimed is:

1. A dental intake device for providing extraoral suction during a dental treatment, comprising:
    a suction hood including:
        an intake opening into which a fluid flows;
        a converging hood inner surface along which the fluid taken in by the intake opening flows; and
        an exhaust opening configured to be operatively connected to a suction source such that the fluid taken in by the intake opening is exhausted via the exhaust opening, wherein the converging hood inner surface continuously converges from the intake opening to the exhaust opening so that the converging hood inner surface forms a truncated conical surface;
    a flow straightening member having a tip and a base opposite to the tip, the flow straightening member being located within the suction hood, the tip of the flow straightening member being closer to the exhaust opening than the intake opening so that the tip is located between the intake opening and the exhaust opening, the flow straightening member having a convex outer surface that is spaced apart from the converging hood inner surface forming a gap between the convex outer surface and the converging hood inner surface, such that all of the fluid taken in by the intake opening flows through said gap; and
    a support that fixes the flow straightening member to the suction hood,
    wherein one part of the support is connected to the convex outer surface at a position which is located between the tip and the base, and
    another part of the support is connected to the converging hood inner surface.

2. The intake device according to claim 1,
    wherein the flow straightening member has a shape selected from a generally egg shape, a generally cone shape, a generally pyramidal shape, and a generally partial spherical shape.

3. The intake device according to claim 1,
    wherein the suction hood is truncated cone-shaped, and a diameter of the intake opening is larger than a diameter of the exhaust opening.

4. The intake device according to claim 1,
    wherein the flow straightening member is completely housed in an inner space of the suction hood.

5. The intake device according to claim 1,
    wherein the base of the flow straightening member outwardly protrudes from the intake opening of the suction hood.

6. The intake device according to claim 5,
    wherein a part of the base of the flow straightening member protrudes from the intake opening and is in a convex shape with a base tip that is located outside of the suction hood.

7. The intake device according to claim 2,
    wherein the suction hood is truncated cone-shaped, and a diameter of the intake opening is larger than a diameter of the exhaust opening.

8. The intake device according to claim 2,
    wherein the support is configured with a plurality of supports, each of the plurality of supports is hemispherically-shaped, and each of the plurality of supports has a vertex and a support base,
    a vertex of each of the plurality of supports is connected to the converging hood inner surface, and
    a support base of each of the plurality of supports is connected to the member outer surface.

9. The intake device according to claim 3,
    wherein the support is configured with a plurality of supports, and each of the plurality of supports is hemispherically-shaped, and each of the plurality of supports has a vertex and a support base,
    a vertex of each of the plurality of supports is connected to the converging hood inner surface, and
    a support base of each of the plurality of supports is connected to the member outer surface.

10. The intake device according to claim 2,
    wherein the base of the flow straightening member outwardly protrudes from the intake opening of the suction hood.

11. The intake device according to claim 3,
    wherein the base of the flow straightening member outwardly protrudes from the intake opening of the suction hood.

12. The intake device according to claim 7,
    wherein the base of the flow straightening member outwardly protrudes from the intake opening of the suction hood.

13. The intake device according to claim 8,
    wherein the base of the flow straightening member outwardly protrudes from the intake opening of the suction hood.

14. The intake device according to claim 9,
    wherein the base of the flow straightening member outwardly protrudes from the intake opening of the suction hood.

15. The intake device according to claim 10,
    wherein a part of the base of the flow straightening member protrudes from the intake opening and is a convex shape with a base tip that is located outside of the suction hood.

16. The intake device according to claim 11,
    wherein a part of the base of the flow straightening member protrudes from the intake opening and is a convex shape with a base tip that is located outside of the suction hood.

17. The intake device according to claim 12,
    wherein a part of the base of the flow straightening member protrudes from the intake opening and is a convex shape with a base tip that is located outside of the suction hood.

18. The intake device according to claim 13,
wherein a part of the base of the flow straightening member protrudes from the intake opening and is a convex shape with a base tip that is located outside of the suction hood.

19. The intake device according to claim 14,
wherein a part of the base of the flow straightening member protrudes from the intake opening and is a convex shape with a base tip that is located outside of the suction hood.

20. The intake device according to claim 1,
wherein the support is configured with a plurality of supports, and each of the plurality of supports is hemispherically-shaped, and each of the plurality of supports has a vertex and a support base a vertex of each of the plurality of supports is connected to the converging hood inner surface, and a support base of each of the plurality of supports is connected to the member outer surface.

* * * * *